US005278053A

United States Patent [19]
Boeck

[11] Patent Number: 5,278,053
[45] Date of Patent: Jan. 11, 1994

[54] METHOD OF PRODUCING A POLYETHER ANTIBIOTIC FROM ACTINOMADURA FIBROSA SP. NOV. NRRL 18348 AND ACTINOMADURA SP. NRRL 18880

[75] Inventor: LaVerne D. Boeck, Brownsburg, Ind.

[73] Assignee: Eli Lilly and Company, Indianapolis, Ind.

[21] Appl. No.: 760,640

[22] Filed: Sep. 16, 1991

[51] Int. Cl.$^5$ .................. C12P 17/18; C12P 19/60; C12N 1/20
[52] U.S. Cl. .................................. 435/119; 435/74; 435/252.1; 435/825; 435/244; 435/118
[58] Field of Search ............... 435/119, 74, 118, 825, 435/252.1, 244

[56] References Cited

U.S. PATENT DOCUMENTS

| | | | |
|---|---|---|---|
| 4,212,942 | 7/1980 | Miyazaki | 435/119 |
| 4,977,083 | 12/1990 | Boeck | 435/71.3 |
| 5,098,834 | 3/1992 | Hamill | 435/74 |

FOREIGN PATENT DOCUMENTS

| | | | |
|---|---|---|---|
| 328303 | 8/1989 | European Pat. Off. | C07H 17/04 |
| 341019 | 11/1989 | European Pat. Off. | C07D 493/10 |

OTHER PUBLICATIONS

Gerhardt et al; "Manual of Methods for General Bacteriology", ASM, 1981, p. 166.
Tsou, H.-R. et al., J. Antibiotics 42:398–406 (1989).
Day, L. E. et al., Bacterial Proc. A31 (1969).
Mateju, J. et al., Folia Microbiol., 33:440–446 (1988).
Boeck, L. D. et al., Proc. Soc. Ind. Microbiol. USA 18:471, 485 (1977).
Boeck, L. D. et al., Abstr. Soc. Inc. Microbiol. USA P27 (1986).
Mertz, F. P. et al., Soc. Ind. Microbiol. USA Poster Session (1986).

Primary Examiner—Irene Marx
Attorney, Agent, or Firm—Steven A. Fontana; Leroy Whitaker

[57] ABSTRACT

Improved processes for producing a polyether antibiotic compound represented by A82810 comprising: (1) cultivating *Actinomadura fibrosa* sp. nov. NRRL 18348 or Actinomadura sp. NRRL 18880, (2) feeding acid hydrolyzed casein at a rate from about 2.50–7.50 gm/L/day, (3) feeding glucose at a rate from about 2.50–7.50 gm/L/day, and (4) feeding propionate at a rate from about 0.50–1.5 gm/L/day to the appropriate culture medium during fermentation, are provided.

24 Claims, No Drawings

METHOD OF PRODUCING A POLYETHER ANTIBIOTIC FROM ACTINOMADURA FIBROSA SP. NOV. NRRL 18348 AND ACTINOMADURA SP. NRRL 18880

BACKGROUND OF THE INVENTION

A polyether antibiotic having the formula:

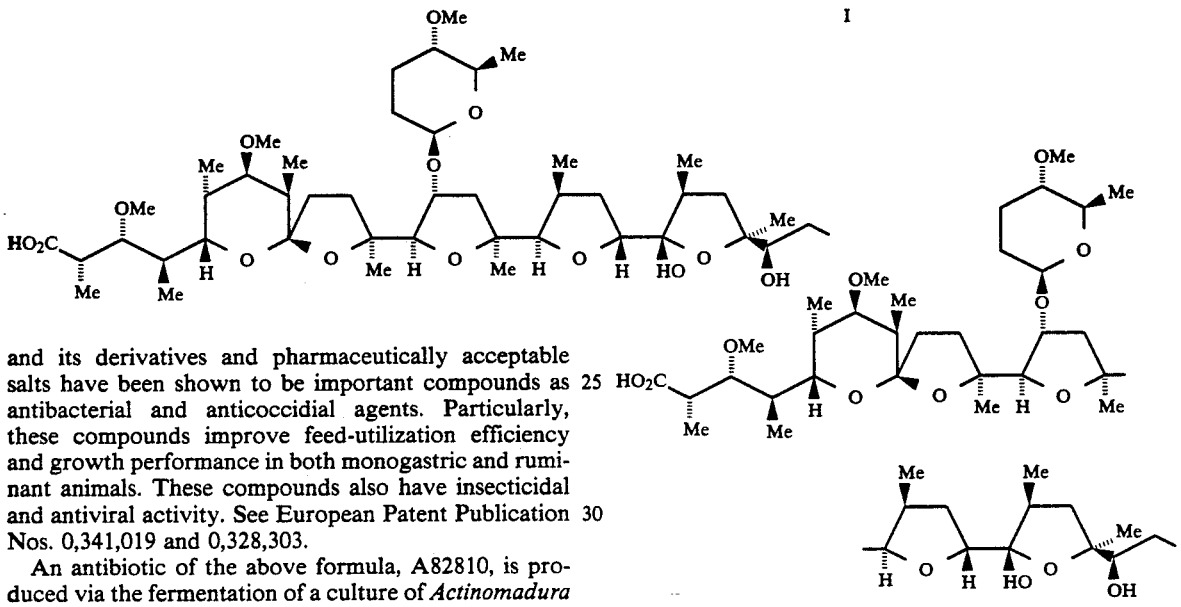

and its derivatives and pharmaceutically acceptable salts have been shown to be important compounds as antibacterial and anticoccidial agents. Particularly, these compounds improve feed-utilization efficiency and growth performance in both monogastric and ruminant animals. These compounds also have insecticidal and antiviral activity. See European Patent Publication Nos. 0,341,019 and 0,328,303.

An antibiotic of the above formula, A82810, is produced via the fermentation of a culture of *Actinomadura fibrosa* sp. nov. NRRL 18348. A culture of *Actinomadura fibrosa* sp. nov. has been deposited and made part of the stock culture collection of the Midwest Area Northern Regional Research Center, Agricultural Research, North Central Region, 1815 North University Street, Peoria, Ill., 61604, from which it is available to the public under the accession number NRRL 18348.

An antibiotic of the above formula is also produced via the fermentation of Actinomadura sp. See EPO 0,328,303. A culture of Actinomadura sp. originally deposited with the American Type Culture Collection, Rockville, Md., having the accession number ATCC 53708, has been redeposited and made part of the stock culture collection of the Midwest Area Northern Regional Research Center. This culture is also available to the public under the accession number NRRL 18880.

The permanency of the deposit of these cultures at the Midwest Area Northern Regional Research Center in Peoria, Ill., and their accessibility to the public are guaranteed in the event a patent is granted. Access to these cultures is available during pendency of this application under 35 U.S.C. §122 and 37 C.F.R. §1.14. All restrictions on the availability to the public of the culture deposited will be irrevocably removed upon granting of the patent.

This invention provides improved processes for the biosynthesis of the polyether antibiotic of the above formula by substantially continuously feeding acid hydrolyzed casein plus propionate, with or without a substantially continuous feed of glucose, to the production medium.

SUMMARY OF THE INVENTION

This invention relates to improvements in methods of producing a polyether antibiotic having the formula:

wherein Me=$CH_3$. This antibiotic, when produced by *Actinomadura fibrosa* sp. nov., NRRL 18348, or a mutant thereof, is known as A82810. A compound of the above formula is also produced by Actinomadura sp., NRRL 18880.

An improved process of this invention, for the production of A82810, comprises substantially continuously feeding acid hydrolyzed casein at a rate from about 2.50 gm/L/day to about 7.50 gm/L/day to an A82810-producing culture starting from about 15 hours to about 35 hours after initiation of the production stage, plus substantially continuously feeding propionate to the same A82810-producing culture at a rate from about 0.50 gm/L/day to about 1.50 gm/L/day starting from about 25 hours to about 70 hours after initiating the production stage, and continuing both feeds throughout the fermentation process. Initiation of the production stage is the time at which vegetative inoculum is added to the production medium, and is also known in the art as the initiation of fermentation. The advantage of this process is that product yields of A82810 are increased.

Another improved process of this invention for A82810 biosynthesis comprises substantially continuously feeding acid hydrolyzed casein and propionate as described above, plus substantially continuously feeding glucose at a rate from about 2.50 gm/L/day to about 7.50 gm/L/day starting from about 15 hours to about 35 hours after initiating the production stage and continuing throughout the fermentation process. This process also provides substantially increased product yields.

This invention further provides for an improved process for the production of A82810 comprising substantially continuous feeds of two-way combinations of acid hydrolyzed casein plus propionate at rates and starting times as described above, and another improved process comprising substantially continuous feeds of threeway combinations of acid hydrolyzed casein, glucose and propionate at rates and starting times as described above. This aspect of the process provides economy of time and material for such continuous feeding of acid hydrolyzed casein, glucose and propionate.

In another improved process of this invention, an antibiotic of the above formula produced by Actinomadura sp., NRRL 18880, is produced by a process comprising cultivating Actinomadura sp. or a mutant thereof in an optimized culture medium containing glucose, acid hydrolyzed casein, blackstrap molasses, MgSO$_4$, CaCO$_3$ and potato dextrin under submerged aerobic fermentation conditions and substantially continuously feeding: acid hydrolyzed casein at a rate from about 3.50 gm/L/day to about 5.50 gm/L/day starting from about 20 to about 25 hours after initiation of the production stage; glucose at a rate from about 3.0 gm/L/day to about 8.0 gm/L/day starting from about 20 to about 25 hours after initiation of the production stage; and propionate from about 0.50 gm/L/day to about 1.0 gm/L/day starting from about 45 hours to about 50 hours after initiation of the production stage, and continuing such feeds throughout the fermentation process. This improvement of the process also provides increased product yields.

DETAILED DESCRIPTION OF THE INVENTION

The polyether antibiotic A82810, having the formula:

salts capable of yielding zinc, sodium, magnesium, calcium, ammonium, chloride, carbonate, sulfate, nitrate and like ions. Particularly, acid hydrolyzed casein serves as a good source of chlorine and sodium.

Essential trace elements necessary for the growth and development of the organism should also be included in the culture medium. Such trace elements commonly occur as impurities in other components of the medium in amounts sufficient to meet the growth requirements of the organism. If foaming is a problem, small amounts (i.e. 0.2 gm/L) of an anti-foam agent such as polypropylene glycol, having a molecular weight of about 2000, may be added to large scale fermentation media if needed.

Examples of preferred concentrations of culture media components are shown in Examples 1 and 2 below.

For production of antibiotic A82810, submerged aerobic fermentation in tanks is preferred. Small quantities of A82810 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger vessel and the production stage of A82810 is initiated. The vegetative inoculum medium can be the same as that used for larger fermentations, but other media are also suitable.

A82810 is produced by the A82810-producing organ-

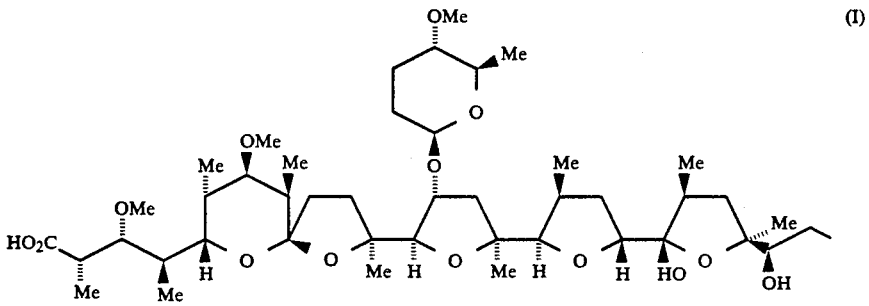

(I)

is produced by culturing a strain of *Actinomadura fibrosa* sp. nov. NRRL 18348 or a mutant thereof, under submerged aerobic fermentation conditions. This method of production is known in the art. See EPO 0,341,019. As was taught in this reference, the culture medium used to grow *Actinomadura fibrosa* culture can be any one of a number of media. However, to maximize the yield benefit from the improved processes of this invention, the culture medium should first be optimized. Optimization is attained by using preferred sources of culture medium components at preferred concentrations.

Preferred carbohydrate sources in large-scale fermentations are glucose and especially potato dextrin, although ribose, xylose, fructose, galactose, mannose, mannitol, and the like can be used.

A preferred nitrogen source is acid hydrolyzed casein although enzyme hydrolyzed casein, yeast, soybean meal, liver meal, meat peptones, fish meal and the like are also useful.

Nutrient inorganic salts which can be incorporated into the culture medium include the customary soluble ism when grown at temperatures between about 25° C. and about 40° C. Using the processes of this invention, an optimum temperature for A82810 production appears to be about 36° C.

As is customary in submerged aerobic culture processes, sterile air is blown into the vessel from the bottom while the medium is stirred with conventional turbine impellors. The maximum oxygen uptake of the fermentation under the conditions used thus far has not exceeded about 0.35 mM/L/minute. In a fully baffled 165-liter fermenter containing approximately 115 liters of broth, an aeration rate of 0.125–1.0 v/v/m with an agitation rate of about 150 rpm to about 450 rpm is sufficient to maintain the level of dissolved oxygen at or above 40% of air saturation at a pressure of about 0.34 atmospheres.

Production of antibiotic A82810 can be followed during the fermentation process by testing samples of the broth for antibiotic activity against organisms known to be sensitive to the antibiotic. One assay organism useful in testing A82810 is *Bacillus subtilis*, ATCC 6633. The bioassay is conveniently performed by the agar-well diffusion test.

Following its production under submerged aerobic fermentation conditions, A82810 and other antibiotics of Formula (I) can be recovered from the fermentation medium by methods used in the fermentation art. See EPO 0,341,019 and 0,328,303.

One improved process of this invention comprises optimizing the culture medium as described above and then substantially continuously feeding acid hydrolyzed casein and propionate. Although propionic acid, or an ester thereof, may be used in the processes of this invention, it is preferred that propionate salts formed from alkali metals or alkaline earth metals be used. Representative suitable salts of propionate include potassium, lithium, cesium, calcium and magnesium, but the sodium salt of propionate is especially preferred. The term "propionate" is used to represent all of the above-mentioned forms thereof.

Substantially continuous feed methods include intermittent to non-stop addition of the feed components: propionate, acid hydrolyzed casein and glucose, added throughout the above-recommended time period, and in amounts which are high enough to increase the yield of an antibiotic of Formula (I) but low enough to avoid inhibition of fermentation. Intervals between additions should not exceed about one to two minutes, but a method of feeding which approaches a steady flow of feed components to production medium is preferred. This preferred method of feeding is denoted by the term "continuous" or "continuously" when used without the limiting term "substantially".

The improvement obtained by this process is illustrated in Table I, which compares the results obtained with a continuous feed of acid hydrolyzed casein versus results obtained with continuous feeds of different rates of sodium propionate and acid hydrolyzed casein.

TABLE I

Effect of Continuous Acid Hydrolyzed Casein Plus Sodium Propionate Feeds on A82810 Biosynthesis

| Acid Hydrolyzed Casein Rate (gm/L/day) | Sodium Propionate Rate[a] (gm/L/day) | A82810 Yield (mcg/mL) |
|---|---|---|
| 5.37[b] | 0.00 | 850 |
| 5.50[c] | 0.40 | 1330 |
| 5.50 | 0.50 | 1600 |
| 5.50 | 0.56 | 1720 |
| 5.50 | 0.91 | 2000 |
| 5.50 | 1.21 | 1750 |

[a]Feeding started about 42 hours after initiating the production stage.
[b]Feeding started about 25 hours after initiating the production stage.
[c]Each of the remaining acid hydrolyzed casein feeds was started about 20 hours after initiating the production stage.

As the results in Table I indicate, the acid hydrolyzed casein and sodium propionate feed increased final A82810 yield by up to 135%.

In the substantially continuous acid hydrolyzed casein and propionate feed process, an acid hydrolyzed casein rate from about 2.50 gm/L/day to about 7.50 gm/L/day is recommended, but a rate from about 4.50 gm/L/day to about 5.50 gm/L/day is preferred for this process. In addition, a propionate rate from about 0.50 gm/L/day to about 1.50 gm/L/day is recommended, but a rate from about 0.85 gm/L/day to about 0.95 gm/L/day is preferred.

In this process, the acid hydrolyzed casein and the propionate is added to the growing A82810-producing culture during the production stage of fermentation. Addition of acid hydrolyzed casein should begin from about 15 hours to about 35 hours after initiating the production stage, and continue until fermentation is terminated. Starting the addition of acid hydrolyzed casein at about 24 hours after initiation of production is preferred.

If propionate is fed to the production medium in the early stages of fermentation, propionate may not be metabolized by the organism and the level of propionate may be raised to inhibitory levels. If propionate feeding is started too late in the antibiotic production process, maximum yields will not be attained. Therefore, addition of propionate should begin from about 25 hours to about 70 hours after initiating the production stage, and continue until fermentation is terminated. Starting the addition of propionate at about 48 hours after initiation of production is preferred.

It is especially preferred, however, to gauge the starting time of the propionate feed on the respiration quotient of the organism $O_2$ consumed/$CO_2$ produced). The propionate feed should begin when the respiration quotient stabilizes at about 1.0. In this context, a respiration quotient of 1.0 denotes that the organism is metabolizing a hexose and, in this fermentation, coincides with initiation of biosynthesis. Under optimum conditions, this frequently occurs at about 40 to about 50 hours after initiation of the production stage. Once the propionate feed is started, the respiration quotient should drop to about 0.90 to about 0.95, and either the propionate or the glucose feed rate should be adjusted to maintain a respiration quotient in this range. If the respiration quotient is below the target range, either the propionate rate should be reduced or the glucose rate should be increased. If respiration quotient is above the target range, either the propionate rate should be increased or the glucose rate should be reduced. It is preferred, however, to adjust the feed rate of propionate to either raise or lower the respiration quotient. If adjustment of the propionate feed rate does not provide the desired result, it may be necessary to adjust the feed rate of glucose.

Acid hydrolyzed casein and propionate may be added by various methods, but they are preferably added as a solution. These feed components may be added in a single solution, but it is preferred that the acid hydrolyzed casein and propionate be added individually so that the rate of feed of each may be independently adjusted.

A preferred process of this invention comprises optimizing the culture medium and substantially continuously feeding acid hydrolyzed casein and propionate as described above, plus substantially continuously feeding glucose. The improvement obtained by this process is illustrated in Table II, which compares sodium propionate feed rates, when added to production media with and without glucose. Each of the following treatments included a continuous feed of acid hydrolyzed casein at a rate from about 4.50 gm/L/day to about 5.50 gm/L/day, starting at about 24 hours after initiation of the production stage and continuing throughout fermentation.

TABLE II

Effect of Continuous Acid Hydrolyzed Casein Plus Sodium Propionate Plus Glucose Feeds on A82810 Biosynthesis

| Sodium Propionate Rate[a] (gm/L/day) | Glucose Rate[b] (gm/L/day) | A82810 Yield (mcg/mL) |
|---|---|---|
| 0.00 | 0.0 | 850 |

TABLE II-continued

Effect of Continuous Acid Hydrolyzed Casein Plus Sodium Propionate Plus Glucose Feeds on A82810 Biosynthesis

| Sodium Propionate Rate[a] (gm/L/day) | Glucose Rate[b] (gm/L/day) | A82810 Yield (mcg/mL) |
|---|---|---|
| 0.91 | 0.0 | 2000 |
| 0.18 | 5.0 | 1550 |
| 0.59 | 5.0 | 2970 |
| 0.86 | 5.0 | 3420 |
| 1.17 | 5.0 | 2930 |
| 1.49 | 5.0 | 2350 |

[a] Feeding started about 65 hours after initiating the production stage
[b] Glucose rates varied about ±0.50 gm/L/day and were continuously fed beginning about 24 hours after initiating the production stage As the results in Table II indicate, the 3-way treatment of continuously fed acid hydrolyzed casein plus sodium propionate plus glucose increased final A82810 yield up to an additional 71% over the 2-way treatment of continuously fed acid hydrolyzed casein and sodium propionate, without glucose. More importantly, the 3-way feed increased final A82810 yield over 300% versus the single feed of acid hydrolyzed casein alone.

In this improved process, a glucose rate from about 2.50 gm/L/day to about 7.50 gm/L/day is recommended, but a rate from about 4.50 gm/L/day to about 5.50 gm/L/day is preferred. These feed rates should be adequate to assist in placing the above-mentioned respiration quotient of the organism in the target range of about 1.0. If this target range is not reached soon after the glucose feed is begun, it may be necessary to adjust the glucose rate so that the target respiration quotient is reached and stabilized before starting the propionate feed. The target respiration quotient should be attained within about 20 to about 30 hours after the initiation of the production stage, but the actual time will depend upon the initial glucose level and the rate of metabolism by the organism after inoculation. Thus, careful monitoring of the glucose feed rate and the resultant respiration quotient is important within this time period.

Glucose, like acid hydrolyzed casein and propionate, is added to the growing A82810-producing culture medium during the production stage of fermentation. Addition of the glucose should begin from about 15 hours to about 35 hours after initiating the production stage and continue until the fermentation is terminated. Starting the addition of glucose at about 24 hours after initiation of production is preferred. Glucose may also be added by various methods, but it is preferably added as a solution. In this process, glucose, acid hydrolyzed casein and sodium propionate may be added in a single solution, but it is preferred that each feed component be added individually so that the rate of feed of each may be independently adjusted.

For the production of an antibiotic of Formula (I), another improved process of this invention comprises optimizing a culture medium containing acid hydrolyzed casein, glucose, blackstrap molasses, $MgSO_4$, $CaCO_3$ and potato dextrin, cultivating Actinomadura sp., NRRL 18880, or a mutant thereof under submerged aerobic fermentation conditions as taught above for Actinomadura fibrosa sp. nov. NRRL 18348, and then substantially continuously feeding acid hydrolyzed casein, glucose and propionate to the cultured medium. Using this improved process, continuous feeding increased yields of the target antibiotic of Formula (I) by an average of over 90%.

In this substantially continuous feed process, the rate of addition of acid hydrolyzed casein, glucose and propionate must be low enough to avoid inhibitory effects on fermentation, but high enough to cause a significant increase in the yield of the target antibiotic. A propionate rate from about 0.50 gm/L/day to about 1.0 gm/L/day is recommended, but a rate from about 0.85 gm/L/day to about 0.95 gm/L/day is preferred. The recommended rate of substantially continuously fed glucose is from about 3.0 gm/L/day to about 8.0 gm/L/day, but a rate from about 4.50 gm/L/day to about 5.50 gm/L/day is preferred. In addition, an acid hydrolyzed casein rate from about 3.50 gm/L/day to about 5.50 gm/L/day is recommended and preferred.

Furthermore, each feed component, propionate, glucose and acid hydrolyzed casein, is added to the growing, antibiotic-producing culture during the production stage of fermentation. Following the general guidelines presented above, addition of propionate should begin from about 45 hours to about 50 hours after initiating the production stage, and continue until the fermentation is terminated. Addition of both glucose and acid hydrolyzed casein should begin from about 20 hours to about 25 hours after initiating the production stage, and also continue until the fermentation is terminated. Each of the feed components may be added by various methods, but they are preferably added as a solution. These components may be added in a single solution, but it is preferred that each feed component be added individually so that the feed rate of each may be independently adjusted.

As is the case with other organisms, the characteristics of the cultures which produce an antibiotic of Formula (I), Actinomadura fibrosa sp. nov. NRRL 18348 and Actinomadura fibrosa sp. nov. NRRL 18880, continue to be subject to variation. Thus, mutants of these strains may be obtained by physical and chemical methods known in the art. For example, other strains can be obtained by treatment with chemicals such as N-methyl-$N^1$-nitro-N-nitrosoguanidine. Use of the above-described processes with natural or induced mutant strains of Actinomadura fibrosa sp. nov. NRRL 18348 and Actinomadura sp. NRRL 18880 which produced an antibiotic of Formula (I) are part of this invention.

In order to illustrate more fully the operation of this invention, the following examples are provided:

EXAMPLE 1

Producing Antibiotic A82810 with Sodium Propionate and Acid Hydrolyzed Casein Continuous Feeds A. Shake-flask Fermentation of A82810

The culture Actinomadura fibrosa sp. nov. NRRL 18348, maintained in liquid nitrogen, was used to inoculate (0.5 mL) a first-stage vegetative medium having the following composition:

| Vegetative Medium I | |
|---|---|
| Ingredient | Amount ( /L) |
| Glucose | 10.0 gm |
| Yeast extract | 5.0 gm |
| Blackstrap molasses | 15.0 gm |
| $MgSO_4$ (anhydrous) | 1.0 gm |
| $CaCO_3$ | 2.0 gm |
| Potato dextrin | 30.0 gm |

Unadjusted pH = 6.3; adjust pH to 7.0 with about 70 mL of 5N NaOH; post.sterilization pH = 6.9.

-continued

| Vegetative Medium I | |
|---|---|
| Ingredient | Amount ( /L) |
| Antifoam added: SAG 471$^a$ (0.2 gm/L) and P-2000$^b$ (0.1 mL/L). | |

$^a$SAG 471 (Union Carbide, Sistersville, WV).
$^b$P-2000 (Dow Chemical Co., Midland, MI).

The inoculated vegetative medium was incubated in a 250-mL wide-mouth Erlenmeyer flask at 37° C. for about 70 hours on a shaker orbiting in a two-inch (5.08 cm) circle at 250 rpm.

B. Tank Fermentation of A82810

In order to provide a larger volume of inoculum, 10 mL of incubated first-stage medium, prepared as described in Section A, was used to inoculate 400 mL of a second-stage vegetative medium having the same composition as that of the first-stage medium. This second stage medium was incubated in a 2-L wide-mouth Erlenmeyer flask at 37° C. for about 48 hours on a shaker orbiting in a two-inch (5.08 cm) circle at 250 rpm.

This second stage vegetative medium (400 mL) was used to inoculate 115 L of sterile production medium having the following composition:

| Production Medium I | |
|---|---|
| Ingredient | Amount ( /L) |
| Glucose | 10.0 gm |
| Acid hydrolyzed casein* | 2.0 gm |
| Blackstrap molasses | 15.0 gm |
| MgSO$_4$ (anhydrous) | 1.0 gm |
| CaCO$_3$ | 2.0 gm |
| Potato dextrin | 50.0 gm |
| Deionized water q.s. to 110 L | |
| Unadjusted pH = 6.8; adjust pH to 7.0 with about 20 mL of 5N NaOH; post-sterilization pH = 6.8. | |
| Antifoam added: SAG 471 (0.2 gm/L) and P-2000 (0.1 mL/L). | |

*Hy-Case amino (Sheffield Chemical Co., Norwich, N.Y.).

The inoculated production medium was allowed to ferment in a 165-L stirred fermentation tank for 6 to 10 days at a temperature of 36° C. A dissolved oxygen level of about 60% of air saturation was maintained, as was a low rpm (150-380) in the stirred vessel.

Beginning about 18 hours after the initiation of the production stage, acid hydrolyzed casein was continuously fed to the production medium at a rate of approximately 5.5 gm/L/day. Beginning at about 45 hours after the initiation of the production stage, sodium propionate was also continuously fed to the fermentation production medium at a rate of approximately 0.91 gm/L/day.

The yield of antibiotic A82810 from the fermentation after about 7 days was 2000 mcg/mL. This yield is substantially greater than the yield of 850 mcg/mL obtained using similar conditions, but without the sodium propionate feed used in this process.

EXAMPLE 2

Producing Antibiotic A82810 with Sodium Propionate, Acid Hydrolyzed Casein and Glucose Continuous Feeds A82810 was produced using the procedures of Example 1 except: 1) first-stage incubation was for 67 hours; 2) second-stage incubation was for 52 hours; 3) potato dextrin amount in this Production Medium II was 60.0 gm/L; 4) unadjusted pH of Production Medium II was 6.5, adjusted to pH 7.0 with about 40 mL of 5N NaOH, and had a post sterilization pH of 7.0; 5) dissolved oxygen level was maintained above 40% of air saturation; and 6) rpm of the stirred fermentation vessel was 200-450.

Furthermore, beginning about 24 hours after the initiation of the production stage, acid hydrolyzed casein was continuously fed to the fermentation medium at a rate of approximately 4.34 gm/L/day and glucose was continuously fed at a rate of approximately 4.39 gm/L/day. Beginning about 42 hours after the initiation of production, sodium propionate was continuously fed to the fermentation medium at a rate of approximately 0.86 gm/L/day. Table III summarizes the biosynthesis results from continuous feed studies.

TABLE III

Effect of Acid Hydrolyzed Casein, Glucose and Sodium Propionate Continuous Feeds to Fermentation Medium on Biosynthesis of A82810 in a Stirred 165-L Bioreactor

| Continuous Feed | Level (gm/L/day) | Biosynthesis (mcg/mL) |
|---|---|---|
| (a) acid hydrolyzed casein | 5.50 | 850 |
| (b) (a) plus sodium propionate | 5.37 + 0.91 | 2000 |
| (c) (b) plus glucose | 4.34 + 4.39 + 0.86 | 3420 |

EXAMPLE 3

Producing an Antibiotic of Formula (I) with Sodium Propionate, Acid Hydrolyzed Casein and Glucose Continuous Feeds via a Culture of *Actinomadura* sp. NRRL 18880.

An antibiotic of Formula (I) was produced by a culture of *Actinomadura* sp. NRRL 18880 using the procedures of Example 2 except: 1) first-stage incubation was for 96 hours; 2) second-stage incubation was for 72 hours; 3) unadjusted pH of Production Medium II was 6.8, adjusted to pH 7.0 with about 25 mL of 5N NaOH, and had a post-sterilization pH of 7.0; 4) dissolved oxygen was maintained above about 60% air saturation; and 5) rpm of the stirred fermentation vessel was 150 at the beginning of the fermentation process and incrementally increased over time to about 450.

Furthermore, acid hydrolyzed casein, glucose and sodium propionate were continuously fed to the fermentation medium. Acid hydrolyzed casein was fed at a rate of approximately 5.09 gm/L/day, glucose was fed at a rate of approximately 5.66 gm/L/day and sodium propionate was fed at a rate of approximately 0.72 gm/L/day. Acid hydrolyzed casein and glucose feeding started about 20 hours after the initiation of the production stage. Sodium propionate feeding started about 42 hours after the initiation of the production stage. The feeding of casein, glucose and sodium propionate continued until a recoverable amount of an antibiotic of Formula (I) was produced.

The yield of antibiotic from this fermentation after about 8 days was 640 mcg/mL. This yield is substantially greater than the yield of 375 mcg/mL obtained under similar conditions, but without the propionate feed used in this process.

I claim:

1. An improved process for producing the antibiotic A82810 having the formula:

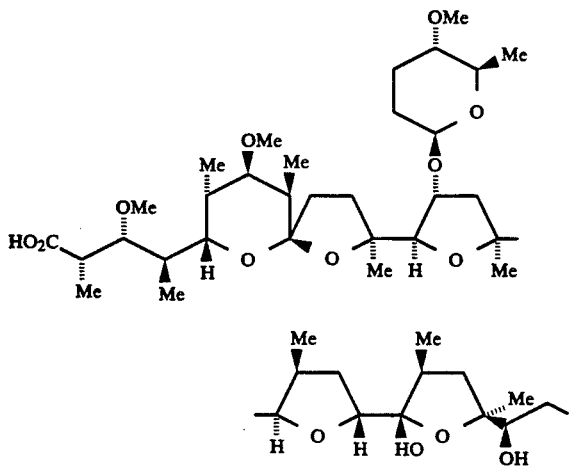

the improvement comprising:
a. substantially continuously feeding acid hydrolyzed casein to an A82810-producing culture of *Actinomadura fibrosa* sp. nov., NRRL 18348, or an A82810-producing mutant thereof, wherein said acid hydrolyzed casein is fed at a rate from about 2.50 gm/L/day to about 7.50 gm/L/day, starting from about 15 hours to about 35 hours after initiation of the production stage and continuing throughout the fermentation until a recoverable amount of antibiotic A82810 is produced;
b. substantially continuously feeding propionate to said culture, wherein said propionate is fed at a rate from about 0.50 gm/L/day to about 1.50 gm/L/day, starting from about 25 hours to about 70 hours after initiating production and continuing throughout the fermentation until a recoverable amount of antibiotic A82810 is produced; and
c. recovering said antibiotic.

2. A process according to claim 1, wherein said feed rate of acid hydrolyzed casein is from about 4.50 gm/L/day to about 5.50 gm/L/day.

3. A process according to claim 1, wherein said feed rate of propionate is from about 0.85 gm/L/day to about 0.95 gm/L/day.

4. A process according to claim 2, wherein said feed rate of propionate is from about 0.85 gm/L/day to about 0.95 gm/L/day.

5. A process according to claim 4, wherein said propionate is sodium propionate.

6. A process according to claim 4, wherein said acid hydrolyzed casein and said propionate are fed in a single solution to said culture.

7. A process according to claim 1 wherein said acid hydrolyzed casein is fed starting about 24 hours after initiating the production stage.

8. A process according to claim 1, wherein said propionate is fed starting about 48 hours after initiating the production stage.

9. A process according to claim 7, wherein said propionate is fed starting about 48 hours after initiating the production stage.

10. A process according to claim 1, wherein glucose is also substantially continuously fed to said culture at a rate from about 2.50 gm/L/day to about 7.50 gm/L/day, starting from about 15 hours to about 35 hours after initiating the production stage and continuing throughout the fermentation until a recoverable amount of antibiotic A82810 is produced.

11. A process according to claim 10, wherein said feed rate of glucose is from about 4.50 gm/L/day to about 5.50 gm/L/day.

12. A process according to claim 11, wherein said feed rate of acid hydrolyzed casein is from about 4.50 gm/L/day to about 5.50 gm/L/day and said rate of propionate is from about 0.85 gm/L/day to about 0.95 gm/L/day.

13. A process according to claim 12, wherein said propionate is sodium propionate.

14. A process according to claim 12, wherein said acid hydrolyzed casein and said glucose are continuously fed in a single solution to said culture.

15. A process according to claim 12, wherein said acid hydrolyzed casein, said glucose and said propionate are continuously fed in a single solution to said culture.

16. A process according to claim 10, wherein said glucose is fed starting about 24 hours after initiating the production stage.

17. A process according to claim 16, wherein said acid hydrolyzed casein is also fed starting about 24 hours after initiating the production stage and said propionate is fed starting about 48 hours after initiating the production stage.

18. A process according to claim 10, wherein said feed rate of glucose is sufficient to maintain the respiration quotient at about 1.0 prior to starting said propionate feed.

19. A process according to claim 18, wherein said propionate is fed starting when the respiration quotient stabilizes at about 1.0 and said propionate rate and said glucose rate is sufficient to maintain said quotient at from about 0.90 to about 0.95 throughout fermentation.

20. A process according to claim 19, wherein said propionate is sodium propionate.

21. A process for producing the antibiotic A82810 having the formula:

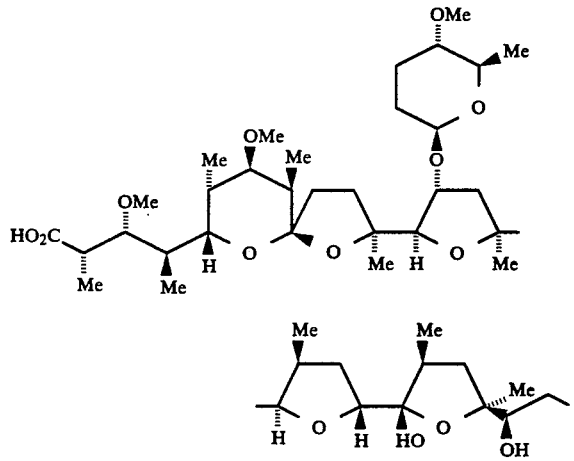

comprising:
a. cultivating *Actinomadura fibrosa* sp. nov. NRRL 18348, or an A82810-producing mutant thereof, in a culture medium containing assimilable sources of carbon, nitrogen, and inorganic salts under submerged aerobic fermentation conditions;
b. substantially continuously feeding acid hydrolyzed casein to said culture medium, wherein said acid hydrolyzed casein is fed at a rate from about 2.50 gm/L/day to about 7.50 gm/L/day, starting from about 15 hours to about 35 hours after initiation of the production stage and continuing throughout fermentation until a recoverable amount of antibiotic A82810 is produced;

c. substantially continuously feeding propionate to said culture medium, wherein said propionate is fed at a rate from about 0.50 gm/L/day to about 1.50 gm/L/day, starting from about 25 hours to about 70 hours after initiation of the production stage and continuing throughout the fermentation until a recoverable amount of antibiotic A82810 is produced; and d. recovering said antibiotic.

22. A process according to claim 21, wherein glucose is also fed to said culture medium at a rate from about 2.50 gm/L/day to about 7.50 gm/L/day, starting from about 15 hours to about 35 hours after initiation of the production stage and continuing throughout the fermentation until a recoverable amount of antibiotic A82810 is produced.

23. A process for producing an antibiotic having the formula:

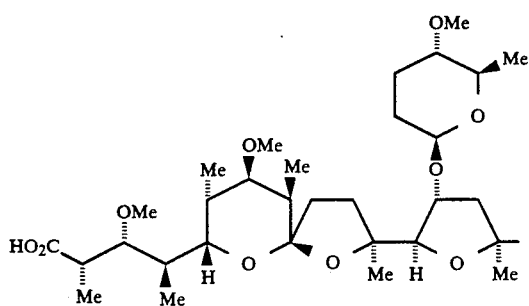

-continued

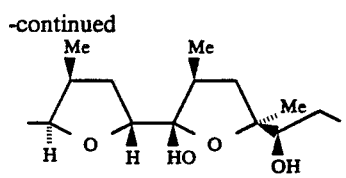

comprising:

a. cultivating a culture of Actinomadura sp., NRRL 18880 or a mutant thereof which produces an antibiotic of said formula in an optimized culture medium containing glucose, acid hydrolyzed casein, blackstrap molasses, MgSO$_4$, CaCO$_3$, and potato dextrin under submerged aerobic fermentation conditions;

b. substantially continuously feeding acid hydrolyzed casein to said culture medium, wherein said acid hydrolyzed casein is fed at a rate from about 3.50 gm/L/day to about 5.50 gm/L/day starting from about 20 to about 25 hours after initiation of the production stage and continuing throughout the fermentation until a recoverable amount of antibiotic of said formula is produced;

c. substantially continuously feeding glucose to said culture medium, wherein said glucose is fed at a rate from about 3.0 gm/L/day to about 8.0 gm/L/day starting from about 20 to about 25 hours after initiation of the production stage and continuing throughout the fermentation until a recoverable amount of antibiotic of said formula is produced; and d. substantially continuously feeding propionate to said culture medium, wherein said propionate is fed at a rate from about 0.50 gm/L/day to about 1.0 gm/L/day starting from about 45 to about 50 hours after initiation of the production stage and continuing throughout the fermentation until a recoverable amount of antibiotic of said formula is produced and recovering said antibiotic.

24. A process according to claim 23, wherein said propionate is sodium propionate.

* * * * *